(12) United States Patent
Byrd et al.

(10) Patent No.: US 9,366,192 B2
(45) Date of Patent: Jun. 14, 2016

(54) HAZARDOUS GAS DETECTION SYSTEM FOR A GAS TURBINE ENCLOSURE

(71) Applicant: General Electric Company, Schenectady, NY (US)

(72) Inventors: Douglas Scott Byrd, Greer, SC (US); Robert Lester Brooks, Greenville, SC (US); Antoine Hochar, Belfort (FR); Christophe Vasinis, Belfort (FR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 388 days.

(21) Appl. No.: 14/176,835

(22) Filed: Feb. 10, 2014

(65) Prior Publication Data

US 2015/0226128 A1 Aug. 13, 2015

(51) Int. Cl.
| | |
|---|---|
| *F02C 7/25* | (2006.01) |
| *F02C 7/24* | (2006.01) |
| *G01N 21/3504* | (2014.01) |
| *G01N 1/22* | (2006.01) |
| *G01N 1/26* | (2006.01) |

(Continued)

(52) U.S. Cl.
CPC ... *F02C 7/25* (2013.01); *F02C 7/24* (2013.01); *G01N 1/2258* (2013.01); *G01N 1/26* (2013.01); *G01N 21/3504* (2013.01); *G01N 33/0063* (2013.01); *G08B 21/14* (2013.01)

(58) Field of Classification Search
CPC .............. F02C 7/25; G01N 1/26; G08B 21/14
USPC ............... 60/39.091, 779; 73/112.01, 112.03, 73/114.77, 863, 863.01, 863.41, 86.51, 73/863.53, 863.71, 864.73, 864.81
See application file for complete search history.

(56) References Cited

U.S. PATENT DOCUMENTS

| | | |
|---|---|---|
| 3,357,257 A | 12/1967 | Herndon et al. |
| 4,051,731 A | 10/1977 | Bohl et al. |
| 4,819,551 A | 4/1989 | Vole |

(Continued)

FOREIGN PATENT DOCUMENTS

EP 2447706 A2 5/2012

OTHER PUBLICATIONS

PCT Search Report and Written Opinion issued on Apr. 20, 2015 in relation to corresponding PCT application PCT/US2015/014969.

(Continued)

*Primary Examiner* — Jason L Vaughan
(74) *Attorney, Agent, or Firm* — Dority & Manning, PA

(57) ABSTRACT

A hazardous gas detection system includes a first and second plurality of air sampling ports in fluid communication with an exhaust duct of a gas turbine enclosure. The first and second plurality of air sampling ports is fluidly connected to a first and second outlet orifice respectfully. A primary sensor is in fluid communication with the first outlet orifice and a secondary sensor is in fluid communication with the second outlet orifice. The primary and secondary sensors generate signals indicative of hazardous gas concentrations in first and second aggregated exhaust air samples. A computing device monitors the hazardous gas concentrations, monitors functionality of the primary and secondary sensors and generates a command signal indicating an operating mode for the gas turbine based on at least one of the hazardous gas concentrations in the first and second aggregated exhaust air samples and the functionality of the primary and secondary sensors.

20 Claims, 6 Drawing Sheets

(51) Int. Cl.
*G01N 33/00* (2006.01)
*G08B 21/14* (2006.01)

(56) References Cited

U.S. PATENT DOCUMENTS

| | | | |
|---|---|---|---|
| 5,024,055 A | 6/1991 | Sato et al. | |
| 5,297,421 A | 3/1994 | Hosonuma et al. | |
| 5,643,077 A | 7/1997 | Ayer | |
| 5,742,516 A | 4/1998 | Olcerst | |
| 5,793,296 A | 8/1998 | Lewkowicz | |
| 5,942,678 A * | 8/1999 | Wettstein | F02C 7/16 165/11.1 |
| 6,110,038 A | 8/2000 | Stern | |
| 6,339,379 B1 | 1/2002 | Argus et al. | |
| 6,425,297 B1 | 7/2002 | Sharp | |
| 6,427,543 B1 * | 8/2002 | Torrison | G01N 1/2273 73/863.33 |
| 6,761,629 B1 * | 7/2004 | Parker | F01D 11/00 114/211 |
| 6,840,086 B2 * | 1/2005 | McCoy | G01M 3/225 340/605 |
| 6,914,532 B2 | 7/2005 | Crooks et al. | |
| 7,389,704 B2 | 6/2008 | Desrochers et al. | |
| 7,632,178 B2 | 12/2009 | Meneely, Jr. | |
| 7,794,526 B2 | 9/2010 | Caro | |
| 8,147,302 B2 | 4/2012 | Desrochers et al. | |
| 8,188,874 B2 | 5/2012 | Calio | |
| 8,291,778 B2 | 10/2012 | Rich | |
| 8,372,186 B2 | 2/2013 | Dobbyn | |
| 9,239,008 B2 * | 1/2016 | Ekanayake | F02C 7/00 |
| 2005/0087027 A1 | 4/2005 | Widmer | |
| 2005/0087028 A1 | 4/2005 | Widmer | |
| 2009/0191803 A1 | 7/2009 | Barrette et al. | |
| 2011/0282501 A1 * | 11/2011 | Martin | F01D 19/00 700/287 |
| 2014/0210639 A1 * | 7/2014 | Skourlis | G01D 4/002 340/870.16 |

OTHER PUBLICATIONS

Co Pending U.S. Appl. No. 14/176,850, filed Feb. 10, 2014.

* cited by examiner

| BOTH SENSORS ACTIVE WITH NO FAULTS | | 1 SENSOR IN FAULT AND 1 SENSOR HEALTHY | | 2 SENSORS IN FAULT |
|---|---|---|---|---|
| HIGH % LEL LEVEL | HIGH-HIGH % LEL LEVEL | HIGH % LEL LEVEL | HIGH-HIGH % LEL LEVEL | |
| 1 SENSOR ALARM | 1 SENSOR ALARM / 2 SENSORS TRIP | 1 SENSOR SHUT DOWN | 1 SENSOR TRIP | TRIP |

HAZARDOUS GAS DETECTION SYSTEM FOR A GAS TURBINE ENCLOSURE

FIELD OF THE INVENTION

The present invention generally involves a hazardous gas detection system. Specifically, the invention relates to a hazardous gas detection system for a gas turbine enclosure.

BACKGROUND OF THE INVENTION

Gas turbines are widely used in industrial, marine, aircraft and power generation operations. A gas turbine includes a compressor section, a combustion section disposed downstream from the compressor section, and a turbine section disposed downstream from the combustion section. In particular configurations the gas turbine is at least partially disposed within an enclosure. Generally, the enclosure protects the gas turbine from resident environmental conditions, reduces acoustic emissions from the gas turbine and insulates the immediate surroundings from heat emanating from the gas turbine during operation.

A ventilation system draws air into the enclosure through one or more inlet ducts, across the turbine and exhausts the air through one or more exhaust ducts, thereby reducing thermal build up within the enclosure and/or removing hazardous gases such as methane or other potentially explosive gases that may leak from the various fuel and/or exhaust connections defined within the enclosure. A hazardous gas detection system is deployed within and/or proximate to the exhaust duct to detect or measure hazardous gas concentrations such as methane or other explosive gas concentrations within the exhaust air flowing through the exhaust duct.

Analysis has shown that concentrations of hazardous gas are highly stratified within the exhaust duct. In other words, the concentration of the hazardous gas is not uniform across an exhaust air flow area defined within the exhaust duct. Therefore, particular hazardous gas detection systems utilize a redundancy method for achieving high reliability and availability of the gas turbine by preventing false alarms and/or controlled shut downs or trips of the gas turbine which may otherwise result from a single point or single sensor failure.

For example, in order to guarantee that two sensors will always be in the hazardous gas flow field particular hazardous gas detection systems utilize three or four sensors arranged in an array along a grid or otherwise spaced across the flow area of the exhaust duct. A computing device or controller receives a signal from each of the sensors that is indicative of the hazardous gas concentration at each sensor location within the exhaust duct flow area.

The computing device utilizes a two out-of three or two out-of four control logic to insure that at least two of the sensors from different locations in the exhaust air flow area are operational and detecting sufficiently high enough concentration levels of the hazardous gas to warrant an alarm, a controlled shut down or trip of the gas turbine. This is required to prevent a trip or shut down due to a single sensor failure and/or a single sensor reading a relatively high concentration of the hazardous gas which may not represent the overall hazardous gas concentration within the exhaust duct flow area.

Multiple sensors placed within the exhaust air flow field results in increased costs and complexity to install, maintain and operate. Proper positioning of each sensor is critical to prevent false alarms and/or unnecessary trips of the gas turbine. However, defining the proper location within the exhaust duct requires highly complicated computational fluid dynamics models which may vary from actual operating conditions. Furthermore, each sensor presents a failure opportunity, thus potentially resulting in an unnecessary trip or shut down of the gas turbine which affects the overall reliability of the system. Therefore, an improved hazardous gas system for a gas turbine enclosure would be useful.

BRIEF DESCRIPTION OF THE INVENTION

Aspects and advantages of the invention are set forth below in the following description, or may be obvious from the description, or may be learned through practice of the invention.

One embodiment of the present invention is a hazardous gas detection system for a gas turbine enclosure. The hazardous gas detection system includes a first air sampling probe that is disposed within an exhaust duct of the gas turbine enclosure. The first air sampling probe includes a first plurality of air sampling ports that are in fluid communication with the exhaust duct and fluidly connected to a first outlet orifice. A primary sensor is disposed or located outside of the exhaust duct. The primary sensor is in fluid communication with the first outlet orifice. The primary sensor generates a first signal that is indicative of a hazardous gas concentration in a first aggregated exhaust air sample collected from the first plurality of air sampling ports. The hazardous gas detection system further includes a second air sampling probe that is disposed within the exhaust duct and that comprises a second plurality of air sampling ports that are in fluid communication with the exhaust duct and that are fluidly connected to a second outlet orifice. A secondary sensor is disposed or located outside of the exhaust duct and in fluid communication with the second outlet orifice. The secondary sensor generates a second signal that is indicative of a hazardous gas concentration in a second aggregated exhaust air sample that is collected from the second plurality of air sampling ports. A computing device is in electronic communication with the primary and secondary sensors and is configured to receive the first and second signals. The computing device is programmed to monitor the hazardous gas concentration in the first and second aggregated exhaust air samples, monitor functionality of the primary and secondary sensors and generate a command signal indicating an operating mode for a gas turbine where the operating mode is based on at least one of the hazardous gas concentration in the first and second aggregated exhaust air samples and the functionality of the primary and secondary sensors.

Another embodiment of the present disclosure is an enclosure for a gas turbine. The enclosure comprises a ventilation system having a plurality of inlet ducts that provide for fluid communication into the enclosure and at least one exhaust duct that provides for fluid communication out of the enclosure. The enclosure further includes a hazardous gas detection system. The hazardous gas detection system includes a first air sampling probe disposed within the exhaust duct. The first air sampling probe includes a first plurality of air sampling ports that are in fluid communication with the exhaust duct and fluidly connected to a first outlet orifice. A primary sensor is disposed outside of the exhaust duct and in fluid communication with the first outlet orifice. The primary sensor generates a first signal indicative of a hazardous gas concentration in a first aggregated exhaust air sample collected from the first plurality of air sampling ports. A secondary sensor is disposed outside of the exhaust duct and is in fluid communication with one of the first outlet orifice or a second outlet orifice of a second air sampling probe disposed within the exhaust duct. When present, the second air sampling probe includes a second plurality of air sampling ports that are in fluid communication with the exhaust duct. The secondary sensor generates a second signal that is indicative of a hazardous gas concentration in a second aggregated exhaust air sample collected from the second plurality of air sampling ports. A computing device is in electronic communication with the primary and secondary sensors. The computing device is programmed to monitor the hazardous gas concentration in the first and second aggregated exhaust air samples, monitor functionality of the first and secondary sensors and to generate a command signal indicating an operating mode for the gas turbine based on at least one of the hazardous gas concentration in the first and second aggregated exhaust air samples and the functionality of the first and secondary sensors.

Another embodiment of the present disclosure includes a power generation facility. The power generating facility includes a gas turbine that is at least partially surrounded by an enclosure having a ventilation system. The ventilation system comprises a plurality of inlet ducts and at least one exhaust duct and a hazardous gas detection system. The hazardous gas detection system includes a first air sampling probe that is disposed within the exhaust duct, The first air sampling probe includes a first plurality of air sampling ports that is fluidly connected in series and in fluid communication with the exhaust duct. The first plurality of air sampling ports is fluidly connected to a first outlet orifice. A primary sensor is disposed outside of the exhaust duct and is in fluid communication with the first outlet orifice. The primary sensor generates a first signal that is indicative of a hazardous gas concentration in a first aggregated exhaust air sample collected from the first plurality of air sampling ports. A second air sampling probe is disposed within the exhaust duct and includes a second plurality of air sampling ports that is fluidly connected in series and in fluid communication with the exhaust duct. The second plurality of air sampling ports is fluidly connected to a second outlet orifice. A secondary sensor is disposed outside of the exhaust duct and in fluid communication with the second outlet orifice. The secondary sensor generates a second signal that is indicative of a hazardous gas concentration in a second aggregated exhaust air sample collected from the second plurality of air sampling ports. A computing device is in electronic communication with the primary and secondary sensors and with the gas turbine. The computing device is programmed to monitor the hazardous gas concentration in the first and second aggregated exhaust air samples, monitor functionality of the primary and secondary sensors and to generate a command signal indicating an operating mode for the gas turbine based on at least one of the hazardous gas concentration in the first and second aggregated exhaust air samples and the functionality of the primary and secondary sensors.

Those of ordinary skill in the art will better appreciate the features and aspects of such embodiments, and others, upon review of the specification.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

DETAILED DESCRIPTION OF THE INVENTION

Figure 1:
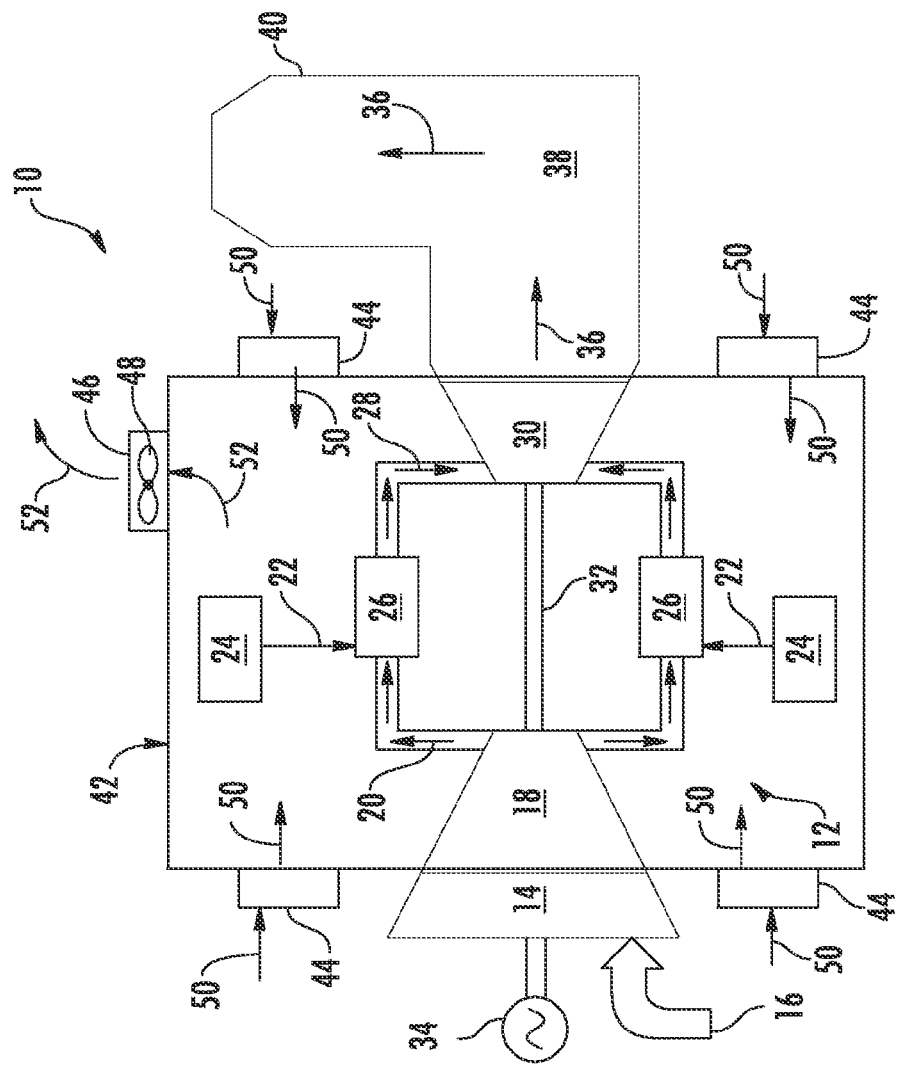
FIG. 1 is a functional block diagram of an exemplary gas turbine that may incorporate various embodiments of the present invention.

Reference will now be made in detail to present embodiments of the invention, one or more examples of which are illustrated in the accompanying drawings. The detailed description uses numerical and letter designations to refer to features in the drawings. Like or similar designations in the drawings and description have been used to refer to like or similar parts of the invention. As used herein, the terms "first", "second", and "third" may be used interchangeably to distinguish one component from another and are not intended to signify location or importance of the individual components. The terms "upstream" and "downstream" refer to the relative direction with respect to fluid flow in a fluid pathway. For example, "upstream" refers to the direction from which the fluid flows, and "downstream" refers to the direction to which the fluid flows.

Each example is provided by way of explanation of the invention, not limitation of the invention. In fact, it will be apparent to those skilled in the art that modifications and variations can be made in the present invention without departing from the scope or spirit thereof. For instance, features illustrated or described as part of one embodiment may be used on another embodiment to yield a still further embodiment. Thus, it is intended that the present invention covers such modifications and variations as come within the scope of the appended claims and their equivalents. Although exemplary embodiments of the present invention will be described generally in the context of a hazardous gas detection system for a land based power generating gas turbine for purposes of illustration, one of ordinary skill in the art will readily appreciate that embodiments of the present invention may be applied to any enclosure ventilation system for any type of gas turbine such as a marine or aircraft gas turbine and are not limited to enclosure ventilation systems for land based power generating gas turbines unless specifically recited in the claims.

Referring now to the drawings, wherein identical numerals indicate the same elements throughout the figures, FIG. 1 provides a functional block diagram of an exemplary power generation facility 10 that may incorporate various embodiments of the present invention. As shown, the power generation facility 10 may include a gas turbine 12 having an inlet section 14. The inlet section 14 may include a series of filters, cooling coils, moisture separators, and/or other devices to purify and otherwise condition a working fluid (e.g., air) 16 entering the gas turbine 12. The working fluid 16 flows to a compressor section where a compressor 18 progressively imparts kinetic energy to the working fluid 16 to produce a compressed working fluid 20.

The compressed working fluid 20 is mixed with a fuel 22 from a fuel source 24 such as a fuel skid to form a combustible mixture within one or more combustors 26. The combustible mixture is burned to produce combustion gases 28 having a high temperature, pressure and velocity. The combustion gases 28 flow through a turbine 30 of a turbine section to produce work. For example, the turbine 30 may be connected to a shaft 32 so that rotation of the turbine 30 drives the compressor 18 to produce the compressed working fluid 20. Alternately or in addition, the shaft 32 may connect the turbine 30 to a generator 34 for producing electricity. Exhaust gases 36 from the turbine 30 flow through an exhaust section 38 that connects the turbine 30 to an exhaust stack 40 that is downstream from the turbine 30. The exhaust section 38 may include, for example, a heat recovery steam generator (not shown) for cleaning the exhaust gases 36 and for extracting additional heat from the exhaust gases 36 prior to release to the environment.

In one embodiment, as shown in FIG. 1, the gas turbine 12 is at least partially surrounded by an enclosure 42 such as a building or other structure. The enclosure 42 may protect the gas turbine 12 from local environmental conditions, reduce acoustic emissions from the gas turbine and/or insulate the immediate surroundings from heat emanating from the gas turbine 12 during operation. The enclosure 42 may at least partially surround the generator 34 and/or may be integrated with the exhaust section 38.

In one embodiment, the enclosure 42 includes a ventilation system. As illustrated in FIG. 1, the ventilation system generally includes at least one inlet duct 44, at least one exhaust duct 46 and one or more fans or blowers 48 for drawing air 50 into the inlet duct 44, through the enclosure 42 and out of the enclosure 42 via the exhaust duct 46. During operation, the air 50 may provide cooling to exterior surfaces of the gas turbine 12. In certain instances, a hazardous or explosive gas such as methane may leak from one or more fuel connections defined within the enclosure 42. The hazardous gas mixes with the air 50 flowing through the enclosure 42 and the mixture flows as exhaust air 52 through the exhaust duct 46 and out of the enclosure 42.

In order to optimize gas turbine availability, reliability and safety, it is critical for operators to have accurate measurements of the concentration of the hazardous gas within the gas turbine enclosure 42 particularly within the exhaust air 52. For example, if the concentration of the hazardous gas within the exhaust air 52 reaches a lower explosive limit (LEL) for a particular hazardous gas such as methane or reaches a predefined percentage of the lower explosive limit for the particular hazardous gas, the gas turbine 12 must be shut down or tripped to address the leak. A false or anomalous reading may result in an unnecessary trip or shut down of the gas turbine 12 at the expense of gas turbine life, power availability and/or loss of profits that may result due to taking the power plant off line.

Figure 2:
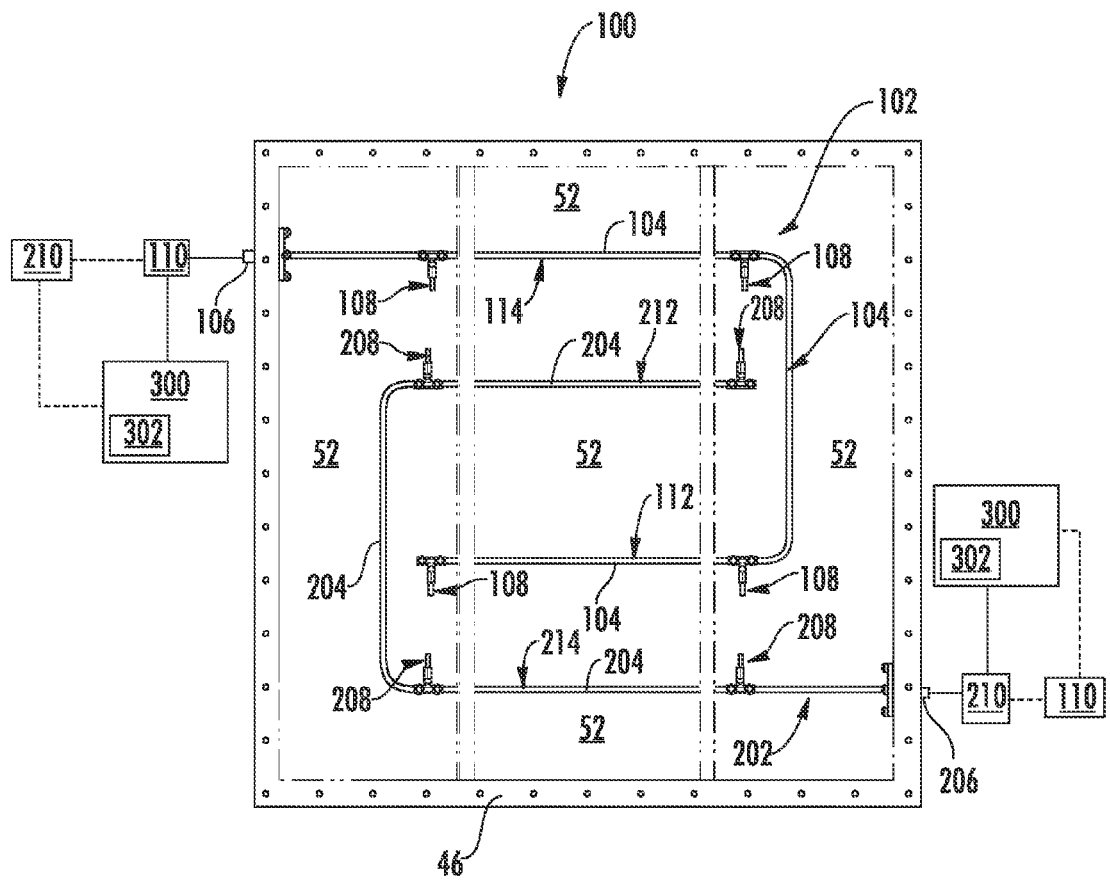
FIG. 2 is a top view of a hazardous gas detection system according to one embodiment of the present invention.

FIG. 2 provides a top view of a hazardous gas detection system 100 and a portion of an exhaust duct 46 as shown in FIG. 1, according to one or more embodiments of the present invention. In one embodiment, the hazardous gas detection system 100, herein referred to as the "system" is mounted within the exhaust duct 46 such that it is in a flow field of exhaust air 52 flowing from within the enclosure 42 proximate to or within the exhaust duct 46.

The system 100 includes a first air sampling probe 102. The first air sampling probe 102 includes one or more fluid conduits or tubes 104 that are in fluid communication with a first outlet orifice 106, a first plurality of inlet orifices or air sampling ports 108 that are in fluid communication with the first outlet orifice 106 via the one or more fluid conduits or tubes 104, and a primary sensor 110 that is in fluid communication with the first plurality of air sampling ports 108 via the first outlet orifice 106. In one embodiment, the first plurality of air sampling ports 108 is connected in series via the tubes 104. The first outlet orifice 106 may extend through a wall of the enclosure 42 or the exhaust duct 46 to provide for fluid communication from the tubes 104 out of the exhaust duct 46 and/or the enclosure 42 to the primary sensor 110.

For redundancy and/or optimized safety and/or availability, the system 100 further includes a second air sampling probe 202. The second air sampling probe 202 includes one or more fluid conduits or tubes 204 in fluid communication with a second outlet orifice 206, a second plurality of inlet orifices or air sampling ports 208 that are in fluid communication with the second outlet orifice 206 via the one or more fluid conduits or tubes 204, and a redundant or secondary sensor 210 that is in fluid communication with the second plurality of air sampling ports 208 via the second outlet orifice 206. In one embodiment, the second plurality of air sampling ports 208 is connected in series via the tubes 204. The second outlet orifice 206 may extend through a wall of the enclosure 42 or the exhaust duct 46 to provide for fluid communication from the tubes 204 out of the exhaust duct 46 and/or the enclosure 42 and to the secondary sensor 210.

In various embodiments, as illustrated in FIG. 2, the system 100 includes a computing device 300. The computing device 300 is in electronic communication with the primary sensor 110 and the secondary sensor 210. As used herein, the term "computing device" includes one or more processors or processing units, system memory, and some form of computer readable media. In one embodiment, the computing device 300 comprises a controller 302 such as a gas turbine controller that is in electronic communication with one or more control systems for affecting an "operating mode" of the gas turbine 12 and/or the power plant facility 10 (FIG. 1).

As used herein, the term "operating mode" may include any operating mode or condition for operating the gas turbine 12. For example, in one embodiment, operating mode includes a normal operating mode wherein the gas turbine is operating without fault such as in a full-speed/full-load condition, a turn-down condition, a full-speed/no-load condition and/or a base-load condition. In another embodiment, operating mode of the gas turbine corresponds to a controlled shut down mode of the gas turbine 12 wherein the various systems controlling the operation of the gas turbine 12 are brought off-line in a controlled or scheduled manner to shut down the gas turbine 12 over a period of time, thus reducing or preventing damage or reduction of life of the various gas turbine components. In another embodiment, operating mode corresponds to a trip of the gas turbine 12. The trip corresponds to a sudden or immediate shut down of the various systems that control the gas turbine so as to bring the gas turbine off-line as soon as possible. However, the trip mode may adversely impact gas turbine life due to potentially extreme and/or non-typical thermal and mechanical stresses which may result from the sudden shut down of those systems.

The computing device 300 may operate in a networked environment using logical connections to one or more remote computers, such as a remote computer. Examples of well-known computing devices that may be suitable for use with aspects of the present disclosure include, but are not limited to, personal computers, server computers, hand-held or laptop devices, multiprocessor systems, microprocessor-based systems, set top boxes, programmable consumer electronics, mobile telephones, network PCs, minicomputers, mainframe computers, distributed computing environments that include any of the above systems or devices, and the like.

The first air sampling probe 102 may be configured to mount within and/or proximate to the exhaust duct 46. For example, as illustrated in FIG. 2, the first air sampling probe 102 may be mounted to the enclosure 42 and/or the exhaust duct 46 via clamps, fasteners and/or may be welded to the exhaust duct 46 and/or the enclosure 42. The first air sampling probe 102 may be configured in any shape. For example, the first air sampling probe 102 may be configured in a generally "U" shape as shown in FIG. 2. In the alternative, the first air sampling probe 102 may be configured to form a square, rectangle, triangle or any curved shape or any combination thereof. In one embodiment, the first air sampling probe 102 comprises a first linear section 112 and a second linear section 114 that runs substantially parallel to the first linear section 112.

The second sampling probe 202 may be configured to mount within and/or proximate to the exhaust duct 46. For example, as illustrated in FIG. 2, the second sampling probe 202 may be mounted to the enclosure 42 and/or the exhaust duct 46 via clamps, fasteners and/or may be welded to the exhaust duct 46 and/or the enclosure 42. The second sampling probe 202 may be configured in any shape. For example, the second sampling probe 202 may be configured in a generally "U" shape as shown in FIG. 2. In the alternative, the second sampling probe 202 may be configured to form a square, rectangle, triangle or any curved shape or any combination thereof. In one embodiment, the second sampling probe 202 comprises a first linear section 212 and a second linear section 214 that runs substantially parallel to the first linear section 212.

In one embodiment, as shown in FIG. 2, the primary sensor 110 and the secondary sensor 210 may be in fluid communication in series or parallel with a single sampling probe 102 or 202 via the first or second outlet orifices 106 or 206. For example, as shown in FIG. 2, the primary and secondary sensors 110, 210 may be in fluid communication with the first sampling probe 102 via the first outlet orifice 106. In the alternative, the primary and secondary sensors 110, 210 may be in fluid communication with the second sampling probe 202 via the second outlet orifice 206. These configurations further reduce the costs of having a second sampling probe and the multiple sampling ports 102, 208.

Figure 3:
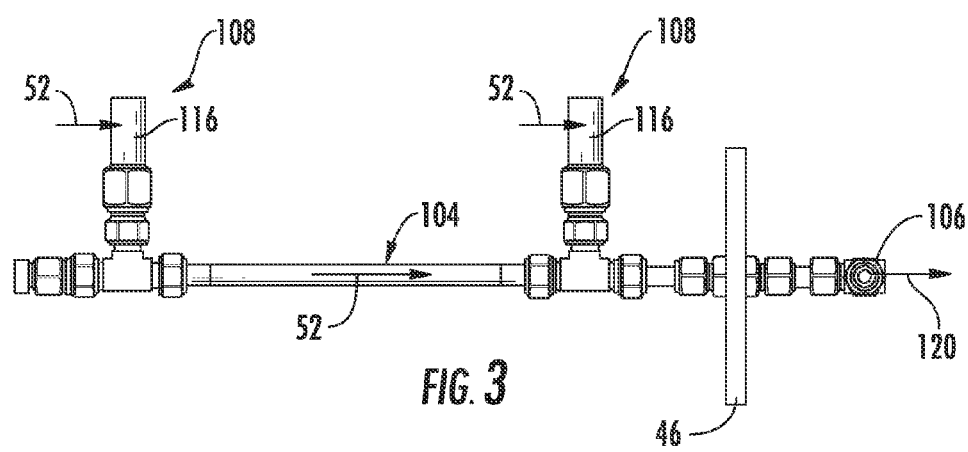
FIG. 3 is an enlarged view of two exemplary air sampling ports of a first plurality of air sampling ports as shown in FIG. 2, according to one embodiment of the present invention.

FIG. 3 provides an enlarged view of two exemplary air sampling ports 108 of the first plurality of air sampling ports 108 as shown in FIG. 2, according to one embodiment. In one embodiment, the first plurality of air sampling ports 108 are passive orifices and provide for fluid communication between the exhaust duct 46 and/or the enclosure 42 and the first outlet orifice 106 via the one or more fluid conduits 104. Flow rate through the first plurality of air sampling ports 108 may be adjustable or fixed to allow a predefined flow rate between the exhaust duct 46 and the primary sensor 110. In particular embodiments, each or at least some of the air sampling ports 108 may be at least partially surrounded by a filter 116 such as a sintered filter to prevent or reduce debris from entering the fluid conduits 104 and thus potentially contaminating the primary sensor 110.

The first plurality of air sampling ports 108 may include any number of air sampling ports 108 greater than two. For example, in one embodiment, as illustrated in FIG. 2, the first plurality of air sampling ports 108 comprises at least four air sampling ports 108. In one embodiment, the plurality of air sampling ports 108 comprises at least two air sampling ports 108 disposed along the first linear section 112 and at least two air sampling ports 108 disposed along the second linear section 114.

Figure 4:
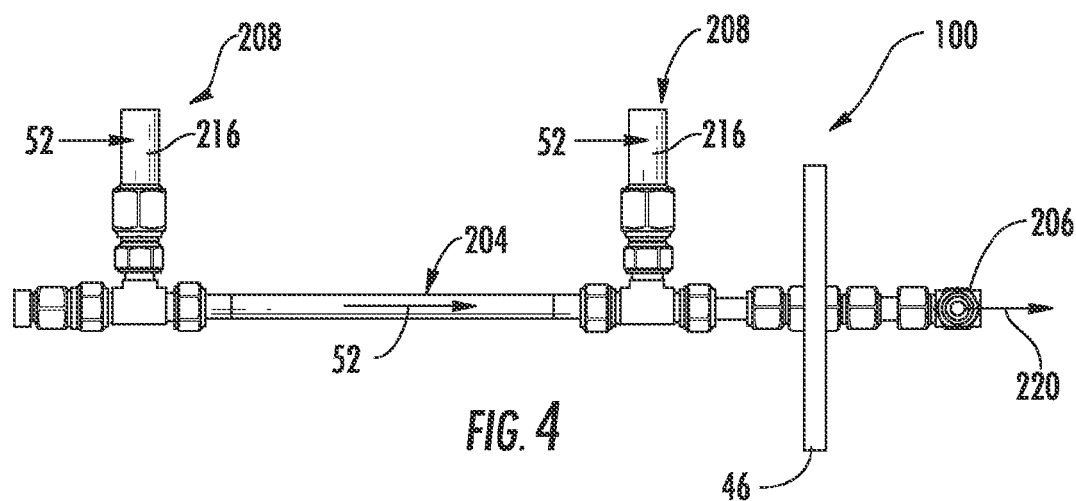
FIG. 4 is an enlarged view of two exemplary air sampling ports of a second plurality of air sampling ports as shown in FIG. 2, according to one embodiment of the present invention.

FIG. 4 provides an enlarged view of two exemplary air sampling ports 208 of the second plurality of air sampling ports 208 as shown in FIG. 2, according to one embodiment. In one embodiment, the second plurality of air sampling ports 208 are passive orifices and provide for fluid communication between the exhaust duct 46 and/or the enclosure 42 and the second outlet orifice 206 via the one or more fluid conduits 204. Flow rate through the second plurality of air sampling ports 208 may be adjustable or fixed to allow a predefined flow rate between the exhaust duct 46 and the secondary sensor 210. In particular embodiments, each or at least some of the second plurality of air sampling ports 208 may be at least partially surrounded by filters 216 such as sintered filters to prevent or reduce debris from entering the fluid conduits 204 and thus potentially contaminating the secondary sensor 210.

The second plurality of air sampling ports 208 may include any number of air sampling ports 208 greater than two. For example, in one embodiment as illustrated in FIG. 2, the second plurality of air sampling ports 208 comprises at least four air sampling ports 208. In one embodiment, the second plurality of air sampling ports 208 comprises at least two air sampling ports 208 disposed along the first linear section 212 and at least two air sampling ports 208 disposed along the second linear section 214.

Figure 5:
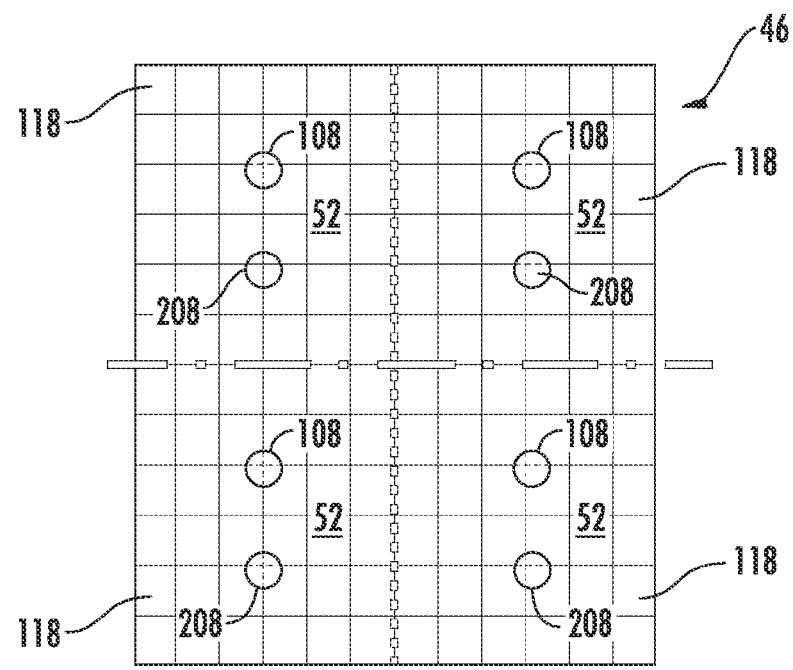
FIG. 5 is a top view of an exemplary exhaust duct as shown in FIG. 2 divided into quadrants, according to one embodiment.

FIG. 5 provides a top view of the exhaust duct 46 as shown in FIG. 2, divided into quadrants 118 according to one embodiment. Analysis and empirical data shows that the concentration of the hazardous gas within the exhaust air 52 is highly stratified or non-uniform within the exhaust duct 46 which may result in an unnecessary alarm or trip of the gas turbine 12. As a result, in one embodiment, the air sampling ports 108 of the first plurality of air sampling ports 108 are positioned such that each quadrant 118 of the exhaust duct 46 includes at least one air sampling port 108 of the first plurality of air sampling ports 108.

In one embodiment, there is one air sampling port 108 of the first plurality of air sampling ports 108 per quadrant 118. Consequently, the flow of exhaust gas 52 through the first outlet orifice 106 (FIG. 3) provides a mixture representing an average concentration of a first aggregated exhaust air sample 120 taken from each quadrant 118 of the exhaust duct 46. This allows for an average measurement of the hazardous gas concentration across the exhaust duct 46 flow area without requiring the primary sensor 110 to be disposed within the exhaust duct 46 and without requiring readings or measurements from multiple sensors, thus decreasing costs associated with installation and maintenance of the system 100. In addition, the placement and/or positioning of the air sampling ports 108 becomes less critical due to the aggregated exhaust air sample 120, thus improving reliability and availability of the gas turbine 12. In one embodiment, as shown in FIG. 5, the second plurality of air sampling ports 208 are positioned such that each quadrant 118 of the exhaust duct 46 includes at least one air sampling port 208 of the second plurality of air sampling ports 208.

In one embodiment, there is one air sampling port 208 of the second plurality of air sampling ports 208 per quadrant 118. Consequently, the flow of exhaust gas 52 through the second outlet orifice 206 (FIG. 4) provides a mixture representing an average concentration of a second aggregated exhaust air sample 220 taken from each quadrant 118 of the exhaust duct 46. This allows for an average measurement of the hazardous gas concentrations across the exhaust duct 46 flow area without requiring the secondary sensor 210 to be disposed within the exhaust duct 46 and without requiring readings or measurements from multiple sensors, thus decreasing costs associated with installation and maintenance of the system 100.

The exact placement of the air sampling ports 208 becomes less critical due to the aggregated exhaust air sample 220, thus improving reliability and availability of the gas turbine 12. In addition, the configuration including the first and second sampling probes 102, 202 disposed within the exhaust duct 46 provides for exhaust air sampling redundancy within each quadrant 118 in case of a single sensor fault and/or loss of functionality of either the primary or secondary sensors 108, 208, thus improving overall reliability of the system 100, availability of the gas turbine 12 and operational safety.

Figures 6, 7:
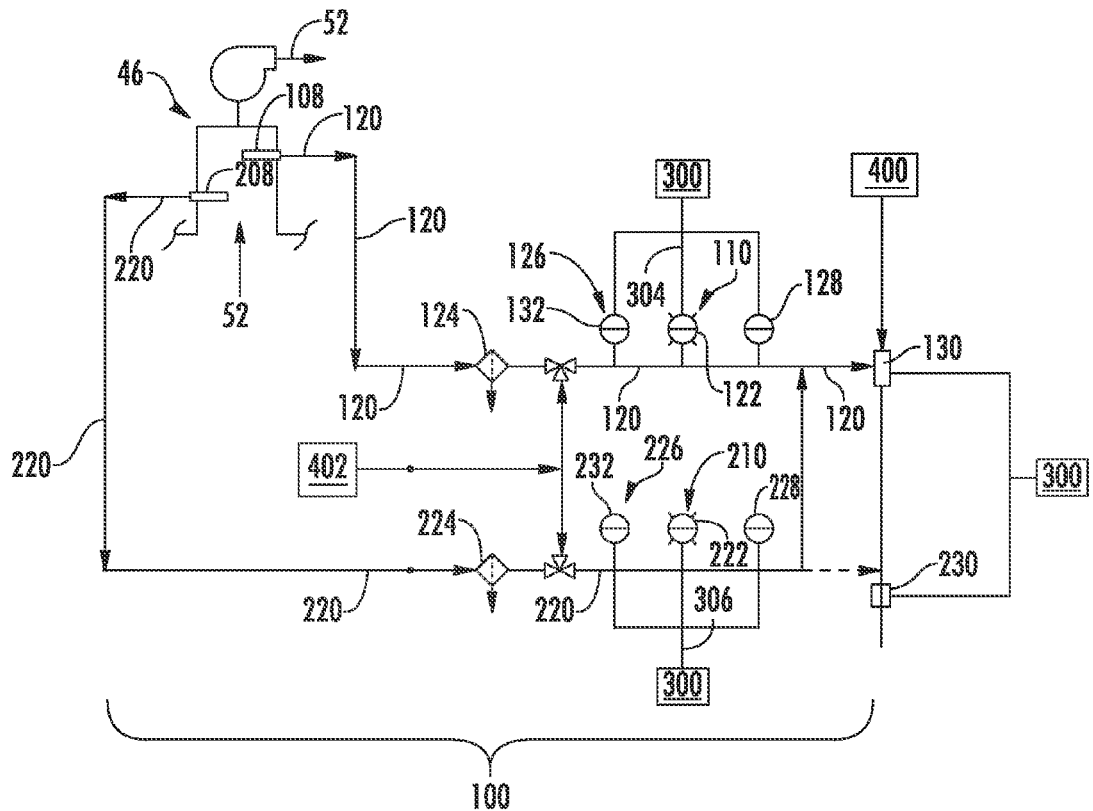
FIG. 6 is a functional block diagram of a hazardous gas detection gas detection system according to one embodiment of the present invention.
FIG. 7 is a table illustrating an exemplary control logic that represents an exemplary fault logic which may be implemented and/or executed via one or more computer executed algorithms executed via a computing device according to one or more embodiments of the present invention.

FIG. 6 provides a functional block diagram of the system 100 including the primary sensor 110 and the secondary sensor 210 according to one embodiment of the present invention. As shown in FIG. 6, the primary sensor 110 and the secondary sensor 210 are disposed outside of the exhaust duct 46, thus reducing the potential for environmental stress on the sensors 110, 210 such as contamination in the exhaust flow and allows for online inspection and maintenance of the system 100. The primary and the secondary sensors 110, 210 are in electronic communication with the computing device 300. One or more fluid conduits or tubes may provide for fluid communication between the first outlet orifice 106 and the primary sensor 110 and the second outlet orifice 206 and the secondary sensor 210.

The primary sensor 110 and the secondary sensor 210 may include any sensor configured and/or designed to detect a hazardous or explosive gas concentration such as methane concentration within the first and second aggregated exhaust air samples 120, 220. In one embodiment, the primary sensor 110 and the secondary sensor 210 includes infrared gas sensors 122, 222. In one embodiment, the infrared gas sensors 122, 222 are set, calibrated and/or configured to detect methane gas concentration within the first and second aggregated exhaust air samples 120, 220.

In particular embodiments, as shown in FIG. 6, the system 100 includes at least one of a flow filter 124 disposed downstream from the first outlet orifice 106 and upstream from the primary sensor 110, a flow switch 126 disposed upstream from the primary sensor 110, a flow indicator 128 disposed downstream from the primary sensor 110 and a first aspirator 130 disposed downstream from the primary sensor 110 to create a negative pressure to pull the first aggregated exhaust air sample 120 through the first plurality of air sampling ports 108 and across the primary sensor 110. In particular embodiments, the system 100 includes a flow sensor 132.

In particular embodiments, the system 100 as shown in FIG. 6, includes at least one of a flow filter 224 disposed downstream from the second outlet orifice 206 and upstream from the secondary sensor 210, a flow switch 226 disposed upstream from the secondary sensor 210 and a flow indicator 228 disposed downstream from the secondary sensor 210. The system 100 may also include a second aspirator 230 disposed downstream from the secondary sensor 210 to create a negative pressure and to pull the second aggregated exhaust air sample 220 through the second plurality of sampling ports 208 and across the secondary sensor 210. In one embodiment, the system 100 further includes a calibration gas supply 402 and/or an instrument air supply 400 for purging, testing and/or calibrating the primary sensor 110 and/or secondary sensor 210. In particular embodiments, the system 100 includes a flow sensor 232.

In one embodiment, flow sensor 132 and/or flow sensor 232 are in electronic communication with the computing device 300. In this manner, the flow sensor 132 and/or 232 communicates a signal to the computing device 300 that is indicative of air flow rate across at least one of the primary sensor 110 and the secondary sensor 210, thus at least partially indicating functionality of the system 100, particularly the aspirator 130 and/or 230. Health or functionality of the primary and secondary sensors 110, 210 may be determined by monitoring sensor signal integrity, receiving a fault signal from the primary or secondary sensors 110, 210, detecting a loss of adequate aspiration within the system 100, detecting signal anomalies from the primary or secondary sensors 110, 210 or by detection of flow switch failure or by any signal, alarm or failure of the system 100 that would indicate loss of sensor functionality or health.

In operation, the fan or blower 48 draws air 50 into the enclosure 42 through the inlet duct 44 and across the gas turbine 12. If a hazardous gas leak is present, such as methane or other explosive gas leak, the hazardous gas is carried out of the enclosure 42 with the exhaust air 52. Multiple samples of the exhaust air 52 are collected from multiple locations from within the flow area of the exhaust duct 46 such as from each quadrant 118 via the first plurality of air sampling ports 108 of the first sampling probe 102 and via the second plurality of air sampling ports 208 of the second sampling probe 202. In particular embodiments, the aspirator 130, 230 may provide a negative pressure within the tubes 104, 204 to pull or draw the exhaust air 52 through the first plurality of air sampling ports 108 and the second plurality of air sampling ports 208 and into the respective tubes 104, 204.

The exhaust air 52 is routed through the respective tubes 104, 204 where each exhaust air sample from each of the respective air sampling ports 108, 208 mixes or combines to provide the first aggregated exhaust air sample 120 at the first outlet orifice 106 and the second aggregated exhaust air sample 220 at the second outlet orifice 206. The first aggregated exhaust air sample 120 and the second aggregated exhaust air sample 220 each represent a total or average concentration of hazardous or explosive gas present within the exhaust duct 46, thus accounting for or representing the stratified concentrations of the hazardous gas within the exhaust duct. In one embodiment, the filters 116, 216 may reduce or prevent contamination from entering the tubes 104, 204 and from flowing downstream towards the first and second outlet orifices 106, 206 and/or towards the primary and secondary sensors 110, 210.

The first aggregated exhaust air sample 120 flows out of the exhaust duct 46 via the first outlet orifice 106 and travels downstream towards the primary sensor 110. The second aggregated exhaust air sample 220 flows out of the exhaust duct 46 via the second outlet orifice 206 and travels downstream towards the secondary sensor 210. In one embodiment, the flow filters 124, 224 may be utilized to filter contamination from the respective first and second aggregated exhaust air samples 120, 220 downstream from the first and second outlet orifices 106, 206 and upstream from the primary and secondary sensors 110, 210.

In one embodiment, the flow switches 126, 226 may be used to monitor and/or control the flow rate of the first and second aggregated exhaust air samples 120, 220 flowing to the respective primary and secondary sensors 110, 210. In one embodiment, the flow indicators 128, 228 may be used to provide a visual indicator of flow of the first and second aggregated exhaust air samples 120, 220 to the respective primary and secondary sensors 110, 210, thus providing a partial indication of functionality and/or operational status of the system 100. In one embodiment, the flow sensors 132, 232 transmit a signal to the computing device 300 that is indicative of air flow rate across at least one of the primary sensor 110 and the secondary sensor 210, thus indicating functionality of the system 100, particularly the aspirator 130 and/or 230.

The primary and secondary sensors 110, 210 measures, senses or otherwise detects the hazardous or explosive gas concentrations of the first and the second aggregated exhaust air samples 120, 220. In one embodiment, the primary sensor 110 generates a first signal 304 that is indicative of a hazardous gas concentration in the first aggregated exhaust air sample 120 and the secondary sensor 210 generates a second signal 306 that is indicative of a hazardous gas concentration in the second aggregated exhaust air sample 220.

The computing device 300 receives the first and second signals 304, 306 and executes one or more algorithms to monitor the hazardous gas concentration in the first and second aggregated exhaust air samples 120, 220 and to monitor or diagnose health or functionality of the primary and secondary sensors 110, 210. In addition, the computing device 300 generates a command signal via the computing device 300 to indicate an operating mode for the gas turbine 12 based on at least one of the hazardous gas concentrations in the first and second aggregated exhaust air samples 120, 220 as indicated by the first and second signals 304, 306, and based upon the health or functionality or the operational condition of the primary and secondary sensors 110, 210.

FIG. 7 provides an exemplary control logic table representing an exemplary fault logic which may be implemented and/or executed via one or more computer executed algorithms executed via the computing device 300 according to one or more embodiments of the present invention. For example, as shown in FIG. 7, when both sensors are active and functioning without fault, the computing device 300 may generate an alarm command signal when one of the primary or secondary sensors 110 or 210 senses hazardous gas concentrations within the corresponding first or second aggregated exhaust air samples 120 or 220 that is below a maximum allowable percentage of the lower explosive limit but above a minimum allowable percentage of the lower explosive limit, represented in FIG. 7 as "High % LEL" under "1 Sensor".

In one embodiment, as shown in FIG. 7, if both sensors 110 and 210 are active and functioning without fault, the computing device 300 may generate an alarm command signal when one of the primary or secondary sensors 110, 210 sense a hazardous gas concentration within the corresponding first or second aggregated exhaust air samples 120, 220 that equals or exceeds a maximum allowable percentage of the lower explosive limit, represented in FIG. 7 as "High-High % LEL" under "1 Sensor". In one embodiment, as shown in FIG. 7, if both sensors 110 and 210 are active and functioning without fault, the computing device 300 may generate a command signal to trip the gas turbine 12 when both the primary and secondary sensors 110, 210 sense hazardous gas concentrations within the first and second aggregated exhaust air samples 120, 220 that equal or exceed a maximum allowable percentage of the lower explosive limit, represented in FIG. 7 as "High-High % LEL" under "2 Sensors".

In one embodiment, as further illustrated in FIG. 7, the computing device may generate a command signal that executes a controlled shut down of the gas turbine 12 if one of the primary and secondary sensors 110 or 210 is healthy or functional and the other primary or secondary sensor 110 or 210 is unhealthy or non-functional and the remaining healthy or functional sensor 110 or 210 senses a hazardous gas concentration within the corresponding first or second aggregated exhaust air sample 120 or 220 that is below a maximum allowable percentage of the lower explosive limit but above a minimum allowable percentage of the lower explosive limit, represented in FIG. 7 as "High % LEL" under "1 Sensor". In one embodiment, the computing device may generate a command signal to trip the gas turbine 12 when one of the primary and secondary sensors 110 or 210 are unhealthy or non-functional and the remaining healthy or functional sensor 110 or 210 senses a hazardous gas concentration within the corresponding first or second aggregated exhaust air sample 120 or 220 that equals or exceeds a maximum allowable percentage of the lower explosive limit, represented in FIG. 7 as "High % LEL" under "1 Sensor". As further illustrated in FIG. 7, the computing device may generate a command signal via the computing device to trip the gas turbine 12 when both the primary and secondary sensors 110 and 210 are unhealthy or non-functional.

Figure 8:
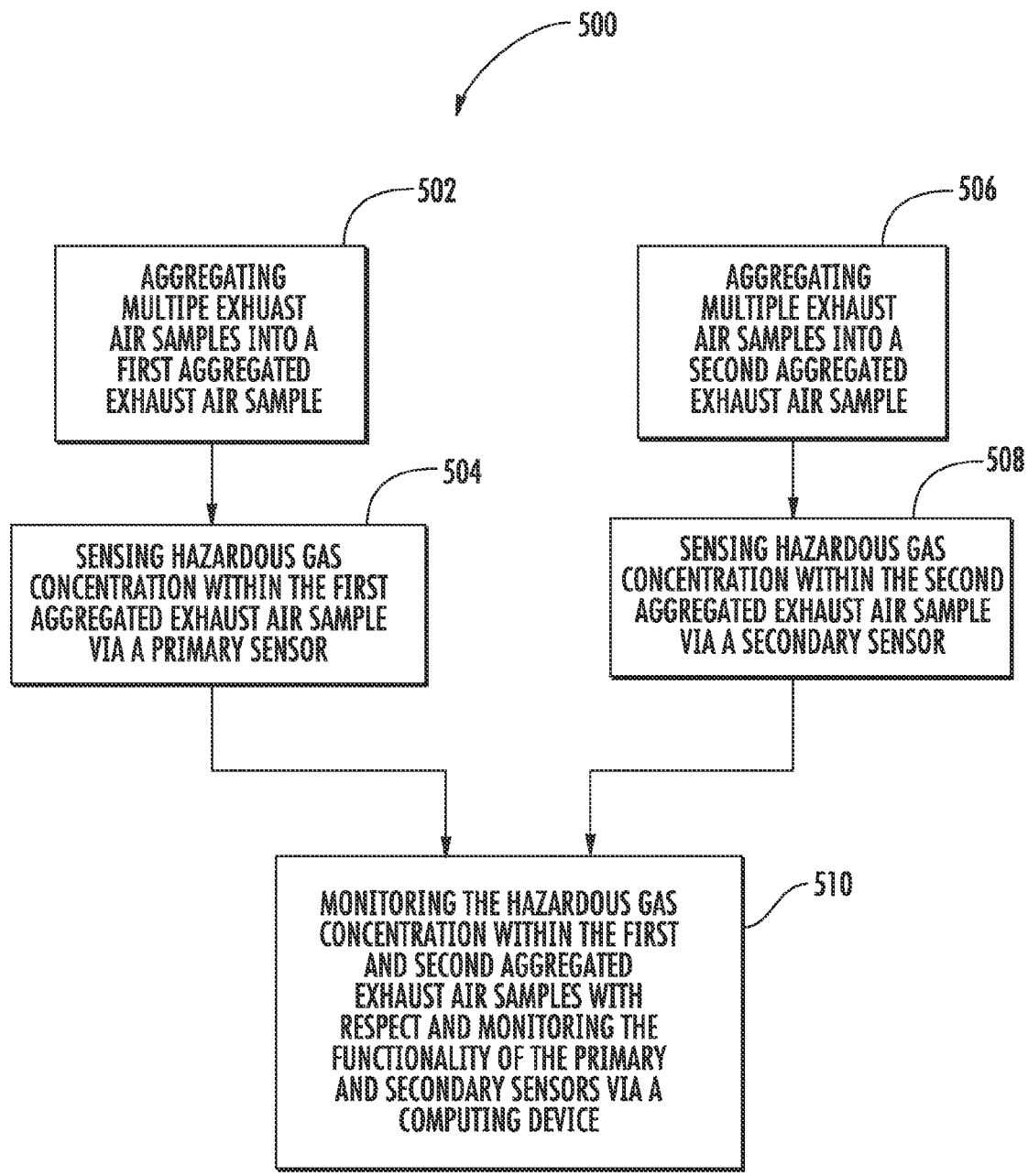
FIG. 8 is a flow chart illustrating an exemplary method for detecting hazardous gas concentrations from an exhaust duct of a gas turbine enclosure according to one embodiment of the present invention.

The various embodiments described herein and illustrated in FIGS. 1 through 7 and as provided in FIG. 8, provide a method for detecting hazardous gas concentrations from the exhaust duct 46 of the gas turbine enclosure 42, herein referred to as method 500. As shown in FIG. 8 at step 502, the method 500 includes aggregating the multiple exhaust air samples collected via the first plurality of sampling ports 108 disposed within the exhaust duct 46 to provide the first aggregated exhaust air sample 120 to the primary sensor 110 disposed outside of the exhaust duct 46. At step 504 the method 500 includes sensing the hazardous gas concentration within the first aggregated exhaust air sample 120 via the primary sensor 110, where the primary sensor 110 communicates a signal that is indicative of the hazardous gas concentration and functionality of the primary sensor 110 to the computing device 300.

At step 506 the method 500 includes aggregating multiple exhaust air samples collected via the second plurality of sampling ports 208 disposed within the exhaust duct 46 to provide the second aggregated exhaust air sample 220 to the secondary sensor 210 which is disposed outside of the exhaust duct 46. At step 508 the method 500 includes sensing the hazardous gas concentration within the second aggregated exhaust air sample 220 via the secondary sensor 210 where the secondary sensor 210 communicates a signal that is indicative of the hazardous gas concentration and functionality of the secondary sensor 210 to the computing device 300. Although steps 502, 504, 506 and 508 are shown as running in parallel, these steps may be run individually and the steps shown in FIG. 8 are not intended as limiting.

At step 510 the method includes monitoring the hazardous gas concentration within the first and second aggregated exhaust air samples 120, 220 with respect to a percentage of the lower explosive limit of the particular hazardous gas or gases sensed within the first and second aggregated exhaust air samples 120, 220 and monitoring the functionality of the primary and secondary sensors 110, 210 via the computing device 330.

In particular embodiments, the step of sensing the hazardous gas concentration within the first aggregated exhaust air sample 120 comprises sensing methane gas concentration within the first aggregated exhaust air sample 120. In one embodiment, the step of sensing the hazardous gas concentration within the second aggregated exhaust air sample 220 comprises sensing methane gas concentration within the second aggregated exhaust air sample 220.

In one embodiment, method 500 further comprises generating a command signal via the computing device 300, for example, by executing one or more algorithms to signal an alarm if both the primary and secondary sensors 110, 210 are functional and one of the primary or secondary sensors 110, 210 sense hazardous gas concentrations within the corresponding first or second aggregated exhaust air samples 120, 220 that is below a maximum allowable percentage of the lower explosive limit but above a minimum allowable percentage of the lower explosive limit. In one embodiment, method 500 further comprises generating a command signal via the computing device 300, for example, by executing one or more algorithms to signal an alarm if both the primary and secondary sensors 110, 210 are functional and one of the primary or secondary sensors 110, 210 sense hazardous gas concentrations within the corresponding first or second aggregated exhaust air samples 120, 220 that equals or exceeds a maximum allowable percentage of the lower explosive limit.

In one embodiment, the method 500 comprises generating a command signal via the computing device, for example, by executing one or more algorithms to trip the gas turbine 12 when both the primary and secondary sensors 110, 210 are functional and both the primary and secondary sensors 110, 210 sense hazardous gas concentrations within the first and second aggregated exhaust air samples 120, 220 that equal or exceed a maximum allowable percentage of the lower explosive limit. In one embodiment, the method 500 comprises generating a command signal via the computing device, for example, by executing one or more algorithms to execute a controlled shut down of the gas turbine 12 if one of the primary and secondary sensors 110, 210 are non-functional and the remaining functional sensor 110 or 210 senses a hazardous gas concentration within the corresponding first or second aggregated exhaust air sample 120 or 220 that is below a maximum allowable percentage of the lower explosive limit but above a minimum allowable percentage of the lower explosive limit.

In one embodiment, method 500 comprises generating a command signal via the computing, for example, by executing one or more algorithms to trip the gas turbine 12 when one of the primary and secondary sensors 110 or 210 are non-functional and the remaining functional sensor 110 or 210 senses a hazardous gas concentration within the corresponding first or second aggregated exhaust air sample 120 or 220 that equals or exceeds a maximum allowable percentage of the lower explosive limit. In one embodiment, the method 500 comprises generating a command signal via the computing device, for example, by executing one or more algorithms to trip the gas turbine 12 when both the primary and secondary sensors 110 and 210 are non-functional.

In one embodiment, the step of monitoring the functionality of the primary and secondary sensors 110, 210 comprises monitoring a flow rate of the first and second aggregated exhaust air samples 120, 220 to the primary and secondary sensors 110, 210. In one embodiment, the step of monitoring the functionality of the primary and secondary sensors 110, 210 comprises monitoring signal integrity of the primary and secondary sensors 110, 210, for example via the computing device 300.

Figure 9:
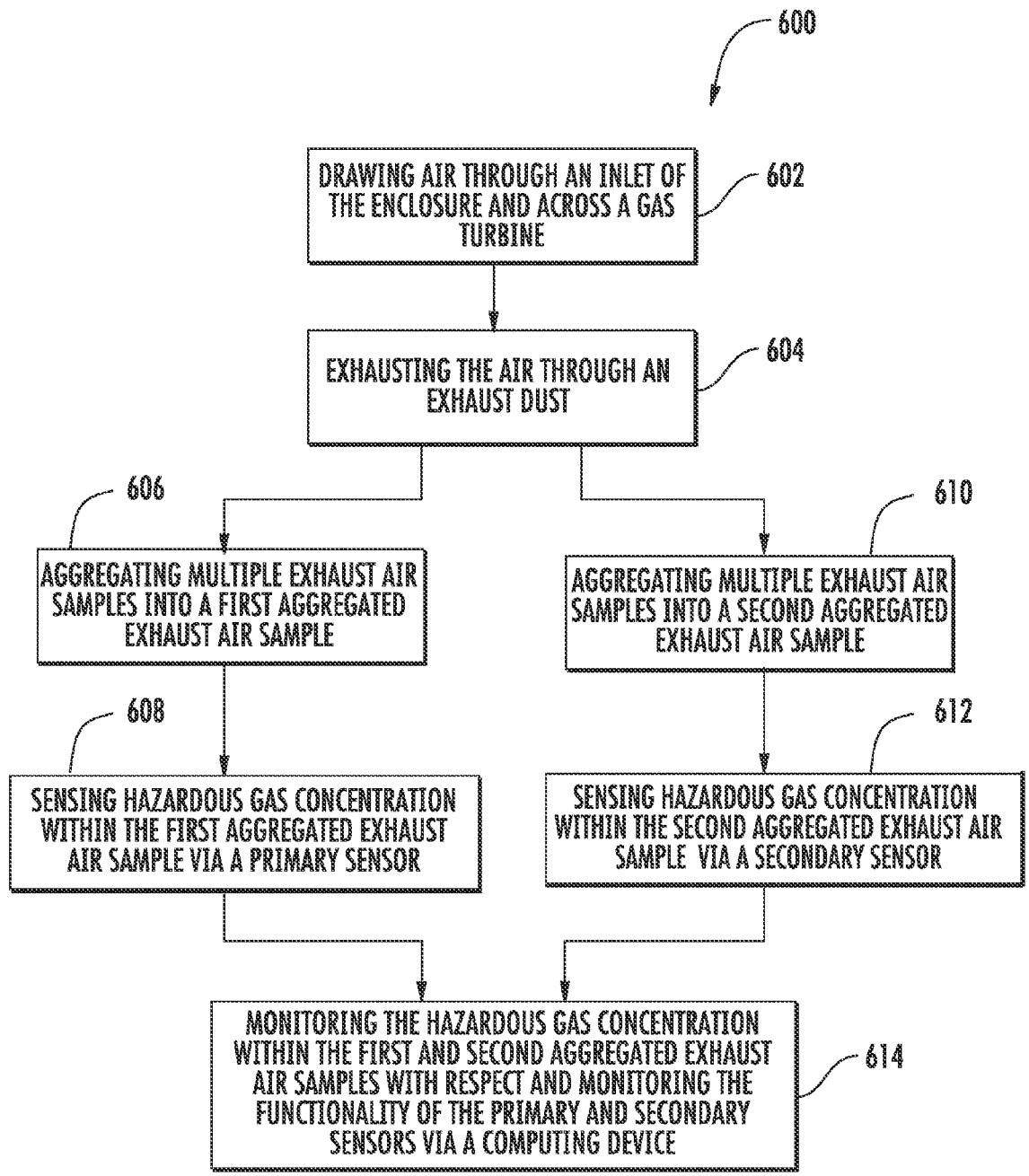
FIG. 9 is a flow chart illustrating an exemplary method for operating a gas turbine based upon the detection of hazardous gas concentrations from an exhaust duct of a gas turbine enclosure according to one embodiment of the present invention.

The various embodiments described herein and illustrated in FIGS. 1 through 7 and as provided in FIG. 9, provide a second exemplary method for detecting hazardous gas within a gas turbine enclosure, herein referred to as method 600. As shown in FIG. 8, at step 602, method 600 includes drawing air 50 through an inlet 44 of the enclosure 42 and across the gas turbine 12. At step 604, method 600 includes exhausting the air 50 as exhaust air 52 through the exhaust duct 46. At step 606, method 600 includes aggregating multiple exhaust air samples 52 collected via the first plurality of sampling ports 108 disposed within the exhaust duct 46 to provide the first aggregated exhaust air sample 120 to the primary sensor 110 disposed outside of the exhaust duct 46. At step 608, method 600 includes sensing hazardous gas concentration within the first aggregated exhaust air sample 120 via the primary sensor 110 where the primary sensor 110 communicates a signal that is indicative of the hazardous gas concentration and functionality of the primary sensor 110 to the computing device 300.

At step 610, method 600 includes aggregating multiple exhaust air samples collected via at least one of the second plurality of sampling ports 208 and the first plurality of sampling ports 108 disposed within the exhaust duct 46 to provide the second aggregated exhaust air sample 220 to the secondary sensor 220 which is disposed outside of the exhaust duct 46. At step 612, method 600 includes sensing hazardous gas concentration within the second aggregated exhaust air sample 220 via the secondary sensor 210 where the secondary sensor 210 communicates a signal that is indicative of the hazardous gas concentration and functionality of the secondary sensor 210 to the computing device 300. At step 614, method 600 includes monitoring the hazardous gas concentration within the first and second aggregated exhaust air samples 120, 220 with respect to a percentage of a lower explosive limit of the particular hazardous gas being sensed and the functionality of the primary and secondary sensors 110, 210 via the computing device. Although steps 606, 608, 610 and 612 are shown as running in parallel, these steps may be run individually and the steps as illustrated in FIG. 9 are not intended as limiting.

In particular embodiments, the steps of sensing the hazardous gas concentration within the first aggregated exhaust air sample 120 and the second aggregated exhaust air sample 220 comprises sensing methane gas concentration within the first and second aggregated exhaust air samples 120 220. In one embodiment, method 600 further comprises generating a command signal via the computing device 300, for example, by executing one or more algorithms to signal an alarm if both the primary and secondary sensors 110, 210 are functional and one of the primary or secondary sensors 110, 210 sense hazardous gas concentrations within the corresponding first or second aggregated exhaust air samples 120, 220 that is below a maximum allowable percentage of the lower explosive limit but above a minimum allowable percentage of the lower explosive limit. In one embodiment, method 600 further comprises generating a command signal via the computing device 300, for example, by executing one or more algorithms to signal an alarm if both the primary and secondary sensors 110, 210 are functional and one of the primary or secondary sensors 110, 210 sense hazardous gas concentrations within the corresponding first or second aggregated exhaust air samples 120, 220 that equals or exceeds a maximum allowable percentage of the lower explosive limit.

In one embodiment, the method 600 comprises generating a command signal via the computing device, for example, by executing one or more algorithms to trip the gas turbine 12 when both the primary and secondary sensors 110, 210 are functional and both the primary and secondary sensors 110, 210 sense hazardous gas concentrations within the first and second aggregated exhaust air samples 120, 220 that equal or exceed a maximum allowable percentage of the lower explosive limit. In one embodiment, method 600 comprises generating a command signal via the computing device, for example, by executing one or more algorithms to execute a controlled shut down of the gas turbine 12 if one of the primary and secondary sensors 110, 210 are non-functional and the remaining functional sensor 110 or 210 senses a hazardous gas concentration within the corresponding first or second aggregated exhaust air sample 120 or 220 that is below a maximum allowable percentage of the lower explosive limit but above a minimum allowable percentage of the lower explosive limit.

In one embodiment, method 600 comprises generating a command signal via the computing, for example, by executing one or more algorithms to trip the gas turbine 12 when one of the primary and secondary sensors 110 or 210 are non-functional and the remaining functional sensor 110 or 210 senses a hazardous gas concentration within the corresponding first or second aggregated exhaust air sample 120 or 220 that equals or exceeds a maximum allowable percentage of the lower explosive limit. In one embodiment, method 600 comprises generating a command signal via the computing device, for example, by executing one or more algorithms to trip the gas turbine 12 when both the primary and secondary sensors 110 and 210 are non-functional.

In one embodiment, the step of monitoring the functionality of the primary and secondary sensors 110, 210 comprises monitoring via the computing device at least one of the flow rate of the first and second aggregated exhaust air samples 120, 220 to the corresponding primary and secondary sensors 110, 210 and signal integrity of the primary and secondary sensors 110, 210.

The various embodiments provided herein, provide various technical advantages over existing hazardous gas detection systems for gas turbine enclosure ventilation systems. For example, each of the first and second plurality of air sampling ports 108, 208 is connected in series to the first and secondary sensors 110, 210 respectively. Therefore, the system 100 only requires one primary sensor or the primary sensor 110 and one backup sensor or the secondary sensor 210 to cover the same cross-sectional area as current multi sensors systems and to provide equivalent or improved reliability. As a result, the system 100 as presented herein reduces assembly time and costs, improves reliability and availability of the gas turbine and prevents unnecessary trips and/or an unscheduled shut down of the gas turbine.

In addition, the hazardous gas detection system 100 as presented herein provides a design that is less affected by stratification of gas contours in the ventilation extract, thus making exact placement of the first and second air sampling ports 108, 208 less critical and improving modeling accuracy for designers. In addition, the ability to continue to operate the gas turbine 12 on a reading or measurement from a single functioning sensor 110, 210 increases availability of the gas turbine while providing optimized safety and reliability of the system 100.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal language of the claims.

What is claimed is:

1. A hazardous gas detection system, comprising:
a first air sampling probe disposed within an exhaust duct of a gas turbine enclosure, the first air sampling probe having a first plurality of air sampling ports in fluid communication with the exhaust duct and fluidly connected to a first outlet orifice;
a primary sensor disposed outside of the exhaust duct and in fluid communication with the first outlet orifice, wherein the primary sensor generates a first signal indicative of a hazardous gas concentration in a first aggregated exhaust air sample collected from the first plurality of air sampling ports;
a second air sampling probe disposed within the exhaust duct, the second air sampling probe having a second plurality of air sampling ports in fluid communication with the exhaust duct and fluidly connected to a second outlet orifice;
a secondary sensor disposed outside of the exhaust duct and in fluid communication with the second outlet orifice, wherein the secondary sensor generates a second signal indicative of a hazardous gas concentration in a second aggregated exhaust air sample collected from the second plurality of air sampling ports; and
a computing device in electronic communication with the primary and secondary sensors, wherein the computing device receives the first and second signals, wherein the computing device is programmed to:
monitor the hazardous gas concentration in the first and second aggregated exhaust air samples;
monitor functionality of the primary and secondary sensors; and
generate a command signal indicating an operating mode for a gas turbine based on at least one of the hazardous gas concentration in the first and second aggregated exhaust air samples and the functionality of the primary and secondary sensors.

2. The hazardous gas detection system as in claim 1, wherein the first plurality of air sampling ports are fluidly connected in series via one or more tubes and the second plurality of air sampling ports are fluidly connected in series via one or more tubes.

3. The hazardous gas detection system as in claim 1, wherein at least one of the primary sensor and the secondary sensor comprises an infrared gas sensor.

4. The hazardous gas detection system as in claim 1, wherein at least one of the primary sensor and the secondary sensor comprises a methane gas sensor.

5. The hazardous gas detection system as in claim 1, further comprising at least one of a fluid filter, a flow switch, a flow indicator, an aspirator and an instrument air supply disposed downstream from at least one of the first air sampling probe and the second air sampling probe.

6. The hazardous gas detection system as in claim 1, further comprising a flow sensor in electronic communication with the computing device, wherein the flow sensor communicates a signal to the computing device indicative of air flow rate across at least one of the primary sensor and the secondary sensor and wherein the command signal is at least partially based on the air flow rate.

7. The hazardous gas detection system as in claim 1, wherein the operating mode for the gas turbine comprises one of a normal operating mode, a controlled shut down mode or a trip mode.

8. The hazardous gas detection system as in claim 1, wherein the operating mode corresponds to a normal operating mode when one of the primary and secondary sensors is fully functional and the hazardous gas concentration from the corresponding fully functional primary or secondary sensor is below a predetermined percentage of a lower explosive limit.

9. The hazardous gas detection system as in claim 1, wherein the operating mode corresponds to a controlled shutdown operating mode when one of the primary and secondary sensors is fully functional and the hazardous gas concentration from the corresponding fully functional primary or secondary sensor is between a minimum predetermined percentage and a maximum predetermined percentage of a lower explosive limit.

10. An enclosure for a gas turbine, comprising:
a ventilation system comprising a plurality of inlet ducts that provide for fluid communication into the enclosure and at least one exhaust duct that provides for fluid communication out of the enclosure; and
a hazardous gas detection system, comprising:
a first air sampling probe disposed within the exhaust duct, the first air sampling probe having a first plurality of air sampling ports in fluid communication with the exhaust duct and fluidly connected to a first outlet orifice;
a primary sensor disposed outside of the exhaust duct and in fluid communication with the first outlet orifice, wherein the primary sensor generates a first signal indicative of a hazardous gas concentration in a first aggregated exhaust air sample collected from the first plurality of air sampling ports;
a secondary sensor disposed outside of the exhaust duct and in fluid communication with one of the first outlet orifice and a second outlet orifice of a second air sampling probe disposed within the exhaust duct, the second air sampling probe having a second plurality of air sampling ports in fluid communication with the exhaust duct, wherein the secondary sensor generates a second signal indicative of a hazardous gas concentration in a second aggregated exhaust air sample collected from the second plurality of air sampling ports; and
a computing device in electronic communication with the primary and secondary sensors, wherein the computing device is programmed to:
monitor the hazardous gas concentration in the first and second aggregated exhaust air samples;
monitor functionality of the primary and secondary sensors; and
generate a command signal indicating an operating mode for the gas turbine based on at least one of the hazardous gas concentration in the first and second aggregated exhaust air samples and the functionality of the primary and secondary sensors.

11. The enclosure as in claim 10, wherein the first plurality of air sampling ports are fluidly connected in series via one or more tubes and the second plurality of air sampling ports are fluidly connected in series via one or more tubes.

12. The enclosure as in claim 10, wherein at least one of the primary sensor and the secondary sensor comprises a methane gas sensor.

13. The enclosure as in claim 10, further comprising at least one of a fluid filter, a flow switch, a flow indicator, an aspirator and an instrument air supply disposed downstream from at least one of the first air sampling probe and the second air sampling probe.

14. The enclosure as in claim 10, further comprising a flow sensor in fluid communication with at least one of the first and second flow sensors and in electronic communication with the computing device, wherein the flow sensor communicates a signal to the computing device indicative of air flow rate across at least one of the primary sensor and the secondary sensor, wherein the command signal is at least partially based on the air flow rate.

15. The enclosure as in claim 10, wherein the operating mode comprises one of a normal operating mode, a controlled shut down mode or a trip mode.

16. The enclosure as in claim 10, wherein the operating mode corresponds to a normal operating mode when one of the primary and secondary sensors is fully functional and the hazardous gas concentration from the corresponding fully functional primary or secondary sensor is below a predetermined percentage of a lower explosive limit.

17. The enclosure as in claim 10, wherein the operating mode corresponds to a controlled shutdown operating mode when one of the primary and secondary sensors is fully functional and the hazardous gas concentration from the corresponding fully functional primary or secondary sensor is between a minimum predetermined percentage and a maximum predetermined percentage of a lower explosive limit.

18. The enclosure as in claim 10, wherein the operating mode corresponds to a trip mode when one of the primary and secondary sensors is fully functional and the hazardous gas concentration from the corresponding fully functional primary or secondary sensor exceeds a maximum predetermined percentage of a lower explosive limit, when both the primary and secondary sensors have failed and when the primary and secondary sensors are fully functional and the hazardous gas concentration exceeds the maximum predetermined percentage of a lower explosive limit.

19. A power generation facility, comprising:
a gas turbine at least partially surrounded by an enclosure, the enclosure having a ventilation system comprising a plurality of inlet ducts and at least one exhaust duct; and
a hazardous gas detection system, comprising:
a first air sampling probe disposed within the exhaust duct, the first air sampling probe having a first plurality of air sampling ports fluidly connected in series and in fluid communication with the exhaust duct, wherein the first plurality of air sampling ports is fluidly connected to a first outlet orifice;
a primary sensor disposed outside of the exhaust duct and in fluid communication with the first outlet orifice, wherein the primary sensor generates a first signal indicative of a hazardous gas concentration in a first aggregated exhaust air sample collected from the first plurality of air sampling ports;
a second air sampling probe disposed within the exhaust duct, the second air sampling probe having a second plurality of air sampling ports fluidly connected in series and in fluid communication with the exhaust duct, wherein the second plurality of air sampling ports is fluidly connected to a second outlet orifice;
a secondary sensor disposed outside of the exhaust duct and in fluid communication with the second outlet orifice, wherein the secondary sensor generates a second signal indicative of a hazardous gas concentration in a second aggregated exhaust air sample collected from the second plurality of air sampling ports; and a computing device in electronic communication with the primary and secondary sensors and with the gas turbine, wherein the computing device is programmed to:
- monitor the hazardous gas concentration in the first and second aggregated exhaust air samples;
- monitor functionality of the primary and secondary sensors; and
- generate a command signal indicating an operating mode for the gas turbine based on at least one of the hazardous gas concentration in the first and second aggregated exhaust air samples and the functionality of the primary and secondary sensors.

20. The power generation facility as in claim 19, wherein the operating mode corresponds to a normal operating mode when one of the primary and secondary sensors is fully functional and the hazardous gas concentration from the corresponding fully functional primary or secondary sensor is below a predetermined percentage of a lower explosive limit, wherein the operating mode corresponds to a controlled shutdown operating mode when one of the primary and secondary sensors is fully functional and the hazardous gas concentration from the corresponding fully functional primary or secondary sensor is between a minimum predetermined percentage and a maximum predetermined percentage of a lower explosive limit, and wherein the operating mode corresponds to a trip mode when one of the primary and secondary sensors is fully functional and the hazardous gas concentration from the corresponding fully functional primary or secondary sensor exceeds a maximum predetermined percentage of a lower explosive limit, or both the primary and secondary sensors have failed, or the primary and secondary sensors are fully functional and the hazardous gas concentration exceeds the maximum predetermined percentage of a lower explosive limit.

* * * * *